United States Patent
Gastner et al.

(10) Patent No.: US 7,279,577 B2
(45) Date of Patent: Oct. 9, 2007

(54) METHOD FOR PRODUCING 2-ANILINO-4,6-DIMETHYLPYRIMIDINE

(75) Inventors: Thomas Gastner, Trostberg (DE); Anita Hölzl, Taufkirchen (DE); Claudia Huber, Altenmarkt (DE); Alfred Mascha, Garching (DE)

(73) Assignee: Degussa AG, Trostberg (DE)

( * ) Notice: Subject to any disclaimer, the term of this patent is extended or adjusted under 35 U.S.C. 154(b) by 542 days.

(21) Appl. No.: 10/504,179

(22) PCT Filed: Feb. 21, 2003

(86) PCT No.: PCT/EP03/01808

§ 371 (c)(1),
(2), (4) Date: Aug. 11, 2004

(87) PCT Pub. No.: WO03/070708

PCT Pub. Date: Aug. 28, 2003

(65) Prior Publication Data

US 2005/0154203 A1    Jul. 14, 2005

(30) Foreign Application Priority Data

Feb. 22, 2002 (DE) ................... 102 07 376

(51) Int. Cl.
*C07D 239/42*      (2006.01)

(52) U.S. Cl. ..................... 544/330
(58) Field of Classification Search ............. 544/330
See application file for complete search history.

(56) References Cited

FOREIGN PATENT DOCUMENTS

| EP | 0 310 550 | 4/1989 |
| EP | 0 717 038 A | 6/1996 |

OTHER PUBLICATIONS

Non-Peptide Corticotropin-Releasing Hormone, Arvanitis, et al. Journal of Meedicinal Chemistry, Amer. Chem. Soc. vol. 42, 1999.
Antibakterielle Wirkstoffe, Kreutzberger, et al., vol. 318, 1985.
Antimykotische Wirkstorfe, XX [1,2,3], Fluoriete 2-(4-Toluidino)pyrimidine, Kreutzberger, et al. Jan.-Feb. 1985, pp. 101-103, vol. 22.

*Primary Examiner*—Deepak Rao
(74) *Attorney, Agent, or Firm*—Fulbright & Jaworski L.L.P.

(57) ABSTRACT

In this method for producing 2-anilino-4,6-dimethylpyrimidine by reacting phenylguanidine and/or one of its salts with acetylacetone the reaction takes place in the presence of water and/or without separating the amounts of water that are formed during the reaction. Phenylguanidine carbonate and phenylguanidine hydrogen carbonate preferably in a water-moist form are used for this reaction which is preferably carried out at pressures between 0.1 and 10 bar and at temperatures between 40 and 180° C. In this manner a finely crystalline product of high purity is obtained in very good yields by a technically simple method.

13 Claims, No Drawings

METHOD FOR PRODUCING 2-ANILINO-4,6-DIMETHYLPYRIMIDINE

This application is a §371 of PCT/EP03/01808 filed Feb. 21, 2003 which claims priority from German Patent Application 102 07 376.7 filed Feb. 22, 2002.

The present invention concerns a method for producing 2-anilino-4,6-dimethyl-pyrimidine which is also referred to as pyrimethanil.

Pyrimethanil is of major importance as a crop protection agent and is used as such as a fungicide in various formulations and combinations of active substances.

Several methods for preparing 2-anilino-pyrimidine derivatives are known in the literature. However, in the mostly older methods the target compound is only obtained in moderate yields using expensive reagents. According to EP-B 224 339 formanilides are for example reacted with 2-methanesulfonylpyrimidine derivatives; DD 151 404 recommends the use of 2-chloro-pyrimidine derivatives and aniline.

In a recent method for preparing 2-anilino-4,6-dimethylpyrimidine, a phenyl-guanidine salt is reacted with acetylacetone without solvent; in order for the reaction to succeed it is important that the reaction water that is formed during the reaction is also removed in a vacuum in addition to the carbon dioxide being formed (EP-A 717 038). The product obtained in this manner accumulates as a melt from which very coarse beige crystals are obtained when it cools down.

However, the overall reproducibility of this process must be regarded as problematic. Thus the content of 2-anilino-4,6-dimethylpyrimidine was evaluated on the basis of HPLC area percentages. However, this method cannot detect many by-products which only occur in the chromatogram after a very long running time due to their large mass. If, in contrast, 2-anilino-4,6-dimethylpyrimidine is quantified by means of an external standard, proportions of non-volatile substances and in particular of polar and high-molecular compounds are also found which have an adverse effect on the purity of the product.

Hence from the described disadvantages of the prior art, the object of the present invention is to provide a method for producing 2-anilino-4,6-dimethylpyrimidine in which phenylguanidine and/or one of its salts is reacted with acetylacetone and in which the compound is obtained in good yields and purities as a finely crystalline powder. In doing so the use of expensive and environmentally questionable substances should be avoided as far as possible.

This object is achieved by carrying out the reaction in the presence of water and/or not separating the water that is formed during the reaction.

Surprisingly and in contrast to the prevailing opinion according to the prior art it has turned out that, especially in the presence of water, it is possible to obtain 2-anilino-4,6-dimethylpyrimidine in high yields and of the highest purity in a finely crystalline form. In this manner a finely crystalline product having the best purity is obtained in very good yields in a technically simple manner under environmentally favourable conditions.

According to the present invention phenylguanidine hydrogen carbonate and/or phenylguanidine carbonate whose preparation is well known from the literature are preferably used as the phenylguanidine component (cf. SKW Trostberg AG company brochure, p. 97 (1978); EP-A 560 726).

With regard to the order of addition it is possible either to firstly place the phenyl-guanidine component in water and subsequently add acetylacetone dropwise or conversely to add the phenylguanidine component to a mixture of water and acetylacetone. The rate of addition can usually be varied over a wide range and is only limited by the ability to withdraw the carbon dioxide that is formed during the reaction. However, it is also possible to simultaneously add all three components.

The amount of water added in the claimed method can be varied in a wide range and can be preferably between 0 and 500% of the mass of the phenylguanidine component used. In the case that no water is added, the water formed during the reaction which is not separated according to the invention is already sufficient for an advantageous reaction process. However, it is more preferable to add additional water to the reaction, in particular at least 5% of the mass, more preferably at least 10% of the mass of the phenylguanidine component. The added amount of water before crystallization is particularly preferably between 50 and 150% of the mass of the phenylguanidine component.

Within the scope of the invention it is regarded as preferable to add the phenyl-guanidine component at a molar ratio relative to acetylacetone of 1:0.8 to 2.0 and in particular 1:1.0 to 1.1. In this connection the respective phenylguanidine salt can also be used according to the invention in a water-moist form and thus prior drying can advantageously be omitted.

Furthermore according to the present invention the reaction can be carried out at a pressure between 0.1 and 10 bar and in a wide temperature range of 40 to 180° C., wherein pressures between 1 and 5 bar and in particular atmospheric pressure as well as temperatures between 80 to 100° C. are regarded as particularly preferred. In these temperature and pressure ranges the reaction time is between a few minutes and 4 hours depending on the feed time. Longer reaction times have no adverse effects whatsoever on product quality and yield.

At the end of the reaction the reaction mixture consists of two liquid phases, namely a water and a product phase. The product can be readily separated from this system and solidifies when it cools down. It is particularly advantageous to cool the two-phase system that is obtained while mixing thoroughly to obtain the product in a finely crystalline form. The cooling rate is also not limiting and can vary within a wide range, temperature steps between 10 and 50° C. per hour being recommended.

The crystals obtained in this manner can be separated from the liquid phase in any conventional manner. A product is usually dried at pressures between 0.1 and 1000 mbar and at temperatures between 30 and 95° C., whereas pressures between 10 and 20 mbar and temperatures between 40 and 70° C. are particularly recommended.

Overall the method according to the invention is characterized by being very simple to carry out technically and furthermore by being very environmentally favourable. Besides, the mother liquor separated after the reaction can be recycled as a solvent for further reactions which additionally underlines the economy of the proposed method.

Amounts of acetylacetone and/or phenylguanidine that may have been added in excess are stable under the selected reaction conditions and can be almost completely separated from the mother liquor after the reaction and reused. Furthermore, it is readily possible to use the mother liquor together with the acetylacetone or phenyl-guanidine component contained therein for further reactions which is favourable for energy-saving and also environmental reasons.

The advantages associated with the method according to the invention are illustrated by the following examples.

EXAMPLES

1. Comparative Example According to EP-A 717 038

Phenylguanidine carbonate (51.18 g, 146 mmol) and acetylacetone (37.7 g, 377 mmol) were heated while stirring in a round bottomed flask with an attached water separator with a reflux cooler in a vacuum of 260 mbar. An aqueous phase began to separate at about 55° C. and carbon dioxide was formed. During the continuous separation of the quantities of water and carbon dioxide that were formed, the temperature was increased to 75° C. within 2 h and the pressure was simultaneously lowered to 190 mbar. The initially inhomogeneous mixture was transformed in this process into an orange-brown, clear and water-free liquid phase. The pressure was then lowered to 100 mbar and the mixture was stirred for a further hour at 95° C. Subsequently the remaining acetylacetone was completely removed at 10 mbar. The remaining mass was poured into a dish where a beige-coloured solid formed as it cooled.

Yield: 53.9 g 2-anilino-4,6-dimethylpyrimidine (73% GC, 66% of theory)

2. Inventive Examples 2.1 Water (15 ml) was placed in a flask with a reflux cooler and dropping funnel and phenylguanidine carbonate (34.1 g, 97.3 mmol) was added. The mixture was heated to 85° C. and acetylacetone (22.6 g, 225.8 mmol) was slowly added dropwise during which carbon dioxide formed after some time. After the carbon dioxide development was completed, it was still stirred for a further 3 hours at 95° C. and then slowly cooled to about 20° C. The suspension was filtered with suction, the product was washed three times with 10 ml water each time and dried in a drying cabinet at 60° C.

Yield: 34.1 g 2-anilino-4,6-dimethylpyrimidine (98.2% GC, 87% of theory)

2.2 Water (10 ml) was placed in a flask with a reflux cooler and dropping funnel and acetylacetone (45.2 g, 451.6 mmol) was placed and then, phenylguanidine carbonate (72.0 g, 205.2 mmol) was slowly added at 85° C. After the carbon dioxide development was completed, it was stirred for a further 3 hours at 95° C., water (50 ml, 90° C.) was then added and it was slowly cooled to 20° C. The mixture was filtered with suction, the product was washed three times with 10 ml water (60° C.) each time and dried in a drying cabinet at 60° C.

Yield: 74.4 g 2-anilino-4,6-dimethylpyrimidine (99.1% GC, 91% of theory)

2.3 Water (10 ml) was placed in a flask with a reflux cooler and dropping funnel and acetylacetone (55 g, 549 mmol) was placed and then, phenylguanidine hydrogen carbonate (98.6 g, 500 mmol) was slowly added at 85° C. After the carbon dioxide development was completed, it was stirred for a further 3 hours at 95° C. and then water (70 ml, 85° C.) was added. The emulsion was slowly cooled to 20° C., then filtered with suction, the product was washed three times with 10 ml water (60° C.) each time and dried in a drying cabinet at 60° C.

Yield: 87.9 g 2-anilino-4,6-dimethylpyrimidine (98.6% GC, 87% of theory)

The invention claimed is:

1. A method comprising reacting phenylguanidine, a phenylguanidine salt or a combination thereof with acetylacetone to produce 2-anilino-4,6-dimethylpyrimidine, wherein the reaction is carried out in the presence of water.

2. The method of claim 1, wherein said phenylguanidine salt is selected from the group consisting of phenylguanidine carbonate and phenylguanidine hydrogen carbonate.

3. The method of claim 1, wherein the reaction is carried out at 0.1 to 10 bar.

4. The method of claim 3, wherein the reaction is carried out at a temperature range of 40 to 180° C.

5. The method of claim 3, wherein the molar ratio of the phenylguanidine component to acetylacetone is between 1:0.8 to 2.0.

6. The method of claim 3, wherein 2-anilino-4,6-dimethylpyrimidine is isolated in a crystalline form.

7. The method of claim 2, wherein said phenylguanidine salt is in a water-moist form.

8. The method of claim 3, wherein the reaction is carried out at 1 to 5 bar.

9. The method of claim 1, wherein the reaction is carried out at atmospheric pressure.

10. The method of claim 4, wherein the reaction is carried out at temperature range of 80 to 100° C.

11. The method of claim 5, wherein said molar ratio is between 1:2.0 to 1.1.

12. The method of claim 6, wherein said isolation is conducted by cooling a two-phase system formed during said reaction.

13. A method comprising reacting phenylguanidine, a phenylguanidine salt or a combination thereof with acetylacetone to produce 2-anilino-4,6-dimethylpyrimidine, wherein water is formed during the reaction, and wherein said formed water is not removed.

* * * * *